United States Patent [19]

Narayanan et al.

[11] Patent Number: 5,424,072
[45] Date of Patent: Jun. 13, 1995

[54] WATER SOLUBLE WETTING AGENT FOR PESTICIDE FORMULATIONS

[75] Inventors: Kolazi S. Narayanan, Palisades Park; Ratan K. Chaudhuri, Butler; Robert B. Login, Oakland, all of N.J.; Sohan L. Paul, Harrow, England

[73] Assignee: ISP Investments Inc., Wilmington, Del.

[21] Appl. No.: 134,936

[22] Filed: Oct. 12, 1993

Related U.S. Application Data

[63] Continuation of Ser. No. 920,082, Jul. 27, 1992, abandoned.

[51] Int. Cl.6 ............................................. A01N 25/24
[52] U.S. Cl. .................................... 424/407; 424/405; 548/543
[58] Field of Search ................. 548/543; 424/405, 407

[56] References Cited

U.S. PATENT DOCUMENTS

| | | | |
|---|---|---|---|
| 3,085,931 | 4/1963 | Darlington | 167/33 |
| 3,290,211 | 12/1966 | Schickedantz | 167/22 |
| 3,864,117 | 2/1975 | Gante et al. | 71/115 |
| 4,276,305 | 6/1981 | Suchy | 424/307 |
| 5,035,859 | 7/1991 | Gu et al. | 422/28 |

FOREIGN PATENT DOCUMENTS 8800184  1/1986  WIPO .................. 548/543

*Primary Examiner*—Thurman K. Page
*Assistant Examiner*—Neil Levy
*Attorney, Agent, or Firm*—Jules E. Goldberg; Joshua J. Ward; William J. Sapone

[57] ABSTRACT

A water based wetting agent uses higher alkyl substituted lactam, anionic surfactant and water to enhance the wetting properties of herbicide and pesticide formulations. The composition is effective in enhancing wetting times, and in some instances increases the formulation effectiveness through enhanced contact, better penetration and lower surface tension. Utilizing a herbicide or pesticide formulation including the wetting agent provides a fast absorption of actives with rapid uptake to promote weed control with no or minimal phytotoxicity at the use levels.

18 Claims, No Drawings

WATER SOLUBLE WETTING AGENT FOR PESTICIDE FORMULATIONS

This is a continuation of application Ser. No. 07/920,082, filed Jul. 27, 1992, abandoned.

TECHNICAL FIELD

This invention relates to wetting agents for pesticide and herbicide formulations and more particularly to water soluble wetting agents containing higher alkyl pyrrolidone, an ionic surfactant and water; optionally lower alkyl pyrrolidone and water soluble film forming polymer are included.

BACKGROUND OF THE INVENTION

Wetting agents are an important part of pesticide and herbicide formulations, as they assure uniform dispersion and proper functioning of the active formulation ingredients. For example, plant surfaces are typically hydrophobic and resist wetting by aqueous sprays, thereby reducing the ability to deposit pesticides and herbicides. For maximum efficacy, wetting of the leaf must be improved by using wetting agents.

Many different products are available for use as wetting agents, in the general classes of anionic, cationic and non-ionic. That there are so many different products available illustrates the diversity of chemistry and tendency for certain surfactant/formulation combinations to be optimum, yielding improved activity as opposed to other surfactants combined with the same formulation. Also, specific interactions of the chosen wetting agent with the selected active ingredients can result in very divergent responses. Determining the best wetting agent can be quite difficult when all interactions are considered.

The selection of an appropriate wetting agent and whether it would be acceptable may turn on the concentration necessary to obtain a certain required wetting effectiveness, and thus the cost for providing the wetting agent in the formulation. Consequently, the search continues for economical wetting agents, usable at low concentrations which provide enhanced pesticide activity via enhanced wetting effectiveness.

SUMMARY OF THE INVENTION

It is an object of the present invention to provide a wetting agent which is water soluble for use in applying aqueous pesticides effectively.

It is a further object to provide a water soluble wetting agent which has high effectiveness at low concentrations.

It is yet another object to provide a wetting agent which provides for rapid uptake to promote rain fastness.

It is yet another object to provide a wetting agent which enhances the promotion of stomatal infiltration with no or minimal phytotoxicity.

These and other objects and advantages of the present invention are achieved by providing a water soluble wetting agent for pesticide and herbicide formulations comprising 0.01 to 90% by weight higher alkyl lactam, 0.01 to 24% anionic surfactant and water. An especially preferred embodiment utilizes a homogenous aqueous solution containing 55% N-octyl-2-pyrrolidone, 14% sodium dodecyl sulfate, and water which can be diluted further to any concentration at less than or equal to 15% of the formulation.

It has been found that in the prescribed combination, the higher alkyl lactam remains soluble, no phase separation occurring. Thus, the wetting agent is uniformly disbursed in the required formulation, providing enhanced effectiveness and wetting ability at low cost. In addition, the inventive wetting agent is totally biodegradable, avoiding aromatic components, ethylene oxide residuals or phosphates.

DETAILED DESCRIPTION OF THE INVENTION

The wetting agent of the present invention contains one or more higher alkyl substituted lactams, an anionic surfactant and water. For purposes of this disclosure the term "higher alkyl" refers to $C_6$ alkyl or higher and the term "lactams" is inclusive of caprolactam, valerolactam and pyrrolidone. The lactams as shown in formula I may be used in the invention.

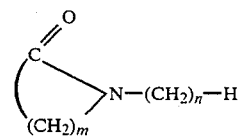

Where $m = 3, 4$ or $5$ and $n \leq 6$.

Preferably, the higher alkyl pyrrolidones of formula II are used.

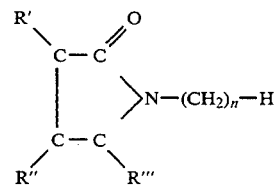

Where $n = 6-20$, $R'$, $R''$ and $R'''$ are H, lower alkyl, alkoxy, cycloalkyl, or aralkyl.

Most preferred are N-octyl-pyrrolidone, N-dodecyl-pyrrolidone or mixtures thereof.

As the anionic surfactant, alkali metal salts of $C_8$–$C_{22}$ aliphatic surfactants such as sodium dodecyl sulfate, sulfonate, alkali metal salts of alkyl aromatic sulfonates, sulfates, ethoxylated versions of the above, alkylphenyl ethoxylated phosphate esters, etc., may be used. The anionic surfactants may form pseudo salts or ion pairs with the higher-alkyl pyrrolidones, and are believed to produce synergistic effects on wetting and surface spreading.

The ranges of the various components may be 0.01 to 90% cyclic lactam, 0.01 to 24% anionic surfactant and water. Preferably, 35 to 65% cyclic lactam, 8 to 16% surfactant and water are used. More preferred is a combination of 39 to 55% higher alkyl pyrrolidone, 10 to 14% surfactant, preferably, sodium dodecyl sulfate, and water. When used as a concentrate, the concentrate can be added to a commercial formulation at the rate of 0.1% to 0.5%.

A particular advantage of the invention is that the cyclic lactams promote solubility of the active ingredients in the formulation increasing uniformity in application together with enhanced wetting. The use of such materials as wetting agents in aqueous compositions would not be expected due to the perceived propensity for phase separation. However, the inventive formulation, utilizing an anionic surfactant with the cyclic lactam, precludes this from occurring.

Various tests were conducted to confirm the efficacy of utilizing the above referenced wetting agent in a pesticide or herbicide formulation.

EXPERIMENT. NO. 1

TABLE I

|  | SA1 | SA2[1] | SS1 | SS2 | Modified SA1 | Modified SA2 | Modified SS2 |
|---|---|---|---|---|---|---|---|
| N-dodecyl pyrrolidone | 53.7 | 40.3 | 52.63 | 51.02 | 33.7 | 20.22 | 20.0 |
| N-octyl pyrrolidone | — | 13.4 | — | — | 0 | 13.15 | 13.0 |
| N-Methyl pyrrolidone |  |  |  |  | 20.0 | 20.22 | 20.0 |
| Sodium Dodecyl sulfate | 13.4 | 13.4 | 13.14 | 12.73 | 13.4 | 13.45 | 13.0 |
| Vinyl Pyrrolidone/ vinyl acetate copolymer | — | — | 2.0 | — | 0 | 0 | 0.0 |
| Polyvinyl pyrollidone/ butene | — | — | — | 5.0 | 0 | 0 | 1.10 |
| H2O | 32.9 | 32.9 | 32.24 | 31.26 | 32.9 | 32.96 | 32.90 |
| TOTAL | 100.0 | 100.0 | 100.0 | 100.0 | 100.0 | 100.0 | 100.0 |

[1]Separated into two layers on storage, however becomes misable or homogeneous on mild mixing. To be mixed before use, see Modified SA2 for completely single phase system.

Referring to Table I, various wetting agent compositions were prepared as described, with the amount given by weight. These were used with various herbicides to determine the efficacy for weed control. To assure homogeneity, it is advantageous to add an optional solvent to the wetting compositions. For example, N-methyl pyrollidone, added to SA1, SA2, and SS2 prevented any tendency to phase separation on standing. The solvent additionally enhanced surface penetration and lowered surface tension which assists in promoting herbicide effectiveness. Other optional ingredients may be added to adjust properties of the inventive wetting agent. For example, other surfactants in addition to the anionic surfactant could be used.

In the first test, SA1 and SA2 were used with two different herbicides in various concentrations. Also, these same herbicides were combined with two known wetting agents, INDUCE, manufactured by Helena Chemical Company which is a mixture of alkylpolyoxyalkane ether, free fatty acids and isopropyl alcohol 90%, constituents ineffective as adjuvants at 10% and also Ortho X-77 which is a blend of alkyl arylpolyoxyethylene glycol and free fatty acids. The herbicides chosen for testing were a systemic herbicide, fluazifop-p-butyl (FUSILADE) butyl 2-[4-(5-trifluoromethyl-2-pyridyloxy) phenoxy]propionate and a contact herbicide, glufosinate (IGNITE) ammonium (3-amino-3-carboxypropyl)-methylphosphinate. Details of the test material concentrations, and application rates are shown in Table II.

TABLE II

| FORMULATIONS | COMMERCIAL ADJUVANTS | | | |
|---|---|---|---|---|
|  | TABLE | INGREDIENTS | CONC. | RATES USED |
| Induce (Helena) | III, IV | Alkylpolyoxy alkane ethers, free fatty acids and isopropyl alcohol | 90% | 0, 0.0625% v/v, 0.125% v/v, |
|  |  | inert ingredients. | 10% | 0.25% |
| Ortho X77* (Valent) | III, IV | Alkylaryl polyoxyethylene glycols free fatty acids and Isopropyl alcohol | 90% | v/v; 20 gal per acre |
|  |  | inert ingredients | 10% |  |
| Complex (Riverside) | VI, VII | Alkylpoly oxyethylene ethers, Polymerized resins and fatty acids | 16.6% | 0, 0.0625% v/v, 0.125% |
|  |  | reacted amines | 5.2% | 0.25% |
|  |  | aromatic petroleum solvents | 4.9% | v/v; 20 gal per acre |
|  |  | inert solvents | 72.3% |  |
| Activate Plus (Riverside) | — | Alkyl aryl poly oxyethylene glycols free fatty acids, Isopropyc alcohol | 90% | 0, 0.1, 0.2, 0.5% v/v |
|  |  | inert ingredients | 10% |  |

TABLE II-continued

COMMERCIAL ADJUVANTS

| FORMULATIONS | TABLE | INGREDIENTS | CONC. | RATES USED |
|---|---|---|---|---|
| Ply (Riverside) | — | Modified poly-p-methene | 85% | 0, 0.5% v/v |
|  |  | aliphatic amines | 5% |  |
|  |  | inert ingredients | 10% |  |
| Silicone (CMR Inc.) | — | Nonylphenoxy polyethoxy ethanol polydimethyl siloxane | 25% | 0, 0.5, 1.15% |
|  |  | inert ingredients | 75% |  |

*When Ortho X-77 was used for evaluation of other low volume herbicides such as Reflex,-use rate of adjuvants were 0, 0.05, 0.1 and 0.2% v/v.

TABLE III

| Treatments: | DAYS AFTER TREATMENT CONTROL % | | | | |
|---|---|---|---|---|---|
|  | 3 | 7 | 21 | 42 | 63 |
| 1. SA1 0.25% | 0 | 0 | 0 | 0 | 0 |
| 2. SA2 0.25% | 0 | 0 | 0 | 0 | 0 |
| 3. Induce 0.25% | 0 | 0 | 0 | 0 | 0 |
| 4. Ortho X-77 0.25% | 0 | 0 | 0 | 0 | 0 |
| 5. Glufosinate 0.5 lb ai/A | 30 | 40 | 50 | 60 | 55 |
| 6. Glufosinate 0.5 lb ai/A + SA1 0.0625% | 30 | 50 | 75 | 80 | 75 |
| 7. Glufosinate 0.5 lb ai/A + SA1 0.125% | 40 | 80 | 100 | 100 | 90 |
| 8. Glufosinate 0.5 lb ai/A + SA1 0.25% | 45 | 85 | 100 | 100 | 90 |
| 9. Glufosinate 0.5 lb ai/A + SA2 0.0625% | 30 | 45 | 65 | 70 | 60 |
| 10. Glufosinate 0.5 lb ai/A + SA2 0.125% | 35 | 50 | 75 | 80 | 75 |
| 11. Glufosinate 0.5 lb ai/A + SA2 0.25% | 40 | 50 | 75 | 80 | 75 |
| 12. Glufosinate 0.5 lb ai/A + Induce 0.0625% | 30 | 45 | 65 | 65 | 50 |
| 13. Glufosinate 0.5 lb ai/A + Induce 0.125% | 35 | 50 | 65 | 70 | 60 |
| 14. Glufosinate 0.5 lb ai/A + Induce 0.25% | 40 | 55 | 70 | 70 | 60 |
| 15. Glufosinate 0.5 lb ai/A + Ortho X-77 + 0.0625% | 35 | 45 | 60 | 65 | 50 |
| 16. Glufosinate 0.5 lb ai/A + Ortho X-77 + 0.125% | 40 | 60 | 70 | 70 | 60 |
| 17. Glufosinate 0.5 lb ai/A + Ortho X-77 + 0.25% | 40 | 65 | 70 | 70 | 60 |
| 18. Fluazifop-p-butyl 0.25 lb ai/A | 5 | 30 | 50 | 50 | 50 |
| 19. Fluazifop-p-butyl 0.25 lb ai/A + SA1 0.0625% | 5 | 45 | 55 | 60 | 60 |
| 20. Fluazifop-p-butyl 0.25 lb ai/A + SA1 0.125% | 5 | 55 | 75 | 85 | 8 |
| 21. Fluazifop-p-butyl 0.25 lb ai/A + SA1 0.25% | 5 | 60 | 75 | 85 | 85 |
| 22. Fluazifop-p-butyl 0.25 lb ai/A + SA2 0.0625% | 5 | 40 | 50 | 55 | 55 |
| 23. Fluazifop-p-butyl 0.25 lb ai/A + SA2 0.125% | 5 | 50 | 60 | 65 | 65 |
| 24. Fluazifop-p-butyl 0.25 lb ai/A + SA2 0.25% | 5 | 50 | 60 | 65 | 65 |
| 25. Fluazifop-p-butyl 0.25 lb ai/A + Induce 0.0625% | 5 | 40 | 50 | 55 | 55 |
| 26. Fluazifop-p-butyl 0.25 lb ai/A + Induce 0.125% | 5 | 45 | 55 | 60 | 60 |
| 27. Fluazifop-p-butyl 0.25 lb ai/A + Induce 0.25% | 5 | 45 | 55 | 60 | 60 |
| 28. Fluazifop-p-butyl 0.25 lb ai/A + Ortho X-77 0.0625% | 5 | 45 | 50 | 55 | 55 |
| 29. Fluazifop-p-butyl 0.25 lb ai/A + Ortho X-77 0.125% | 5 | 50 | 60 | 65 | 65 |
| 30. Fluazifop-p-butyl 0.25 lb ai/A + Ortho X-77 0.25% | 5 | 50 | 60 | 65 | 65 |
| 31. Untreated control | 0 | 0 | 0 | 0 | 0 |

TABLE IV

| Treatments: | DAYS AFTER TREATMENT CONTROL % | | | | |
|---|---|---|---|---|---|
|  | 3 | 7 | 21 | 42 | 63 |
| 1. SA1 0.25% | 0 | 0 | 0 | 0 | 0 |
| 2. SA2 0.25% | 0 | 0 | 0 | 0 | 0 |
| 3. Induce 0.25% | 0 | 0 | 0 | 0 | 0 |
| 4. Ortho X-77 0.25% | 0 | 0 | 0 | 0 | 0 |
| 5. Glufosinate 0.5 lb ai/A | 40 | 50 | 60 | 55 | 40 |
| 6. Glufosinate 0.5 lb ai/A + SA1 0.0625% | 50 | 75 | 80 | 75 | 70 |
| 7. Glufosinate 0.5 lb ai/A + SA1 0.125% | 60 | 90 | 100 | 90 | 90 |
| 8. Glufosinate 0.5 lb ai/A + SA1 0.25% | 60 | 90 | 100 | 90 | 90 |
| 9. Glufosinate 0.5 lb ai/A + SA2 0.0625% | 45 | 60 | 70 | 65 | 60 |
| 10. Glufosinate 0.5 lb ai/A + SA2 0.125% | 50 | 80 | 90 | 85 | 75 |
| 11. Glufosinate 0.5 lb ai/A + SA2 0.25% | 50 | 80 | 90 | 85 | 75 |
| 12. Glufosinate 0.5 lb ai/A + Induce 0.0625% | 50 | 70 | 75 | 70 | 60 |
| 13. Glufosinate 0.5 lb ai/A + Induce 0.125% | 60 | 80 | 85 | 80 | 70 |
| 14. Glufosinate 0.5 lb ai/A + Induce 0.25% | 60 | 80 | 90 | 85 | 70 |
| 15. Glufosinate 0.5 lb ai/A + Ortho X-77 + 0.0625% | 50 | 70 | 75 | 70 | 60 |
| 16. Glufosinate 0.5 lb ai/A + Ortho X-77 + 0.125% | 60 | 80 | 85 | 80 | 70 |
| 17. Glufosinate 0.5 lb ai/A + Ortho X-77 + 0.25% | 60 | 80 | 100 | 90 | 85 |
| 31. Untreated control | 0 | 0 | 0 | 0 | 0 |

The results of the test are shown in Table III for testing on Bahia grass and Table IV for Broadleaf weed control. The control percent is identified under the columns signifying the number of days into the test period, i.e., after 3, 7, 21, 42 or 63 days. Broadleaf weeds include camphor weed, florida pusley, jerusalem oak, lambsquarters, pigweed, spanish needles and tea weed. For conditions of field evaluation see date summarized in Table V.

TABLE V

| | |
|---|---|
| Weather | clear |
| Humidity | 50% |
| Wind velocity | calm |
| Water source | well |
| pH | 7.1 |
| Volume of spray | 20 CPA - gallons per acre |
| Spray pressure | 35 psi |
| Source of pressure | compressed air |
| Nozzle type/size | Teejet tips 8001 |
| Nozzle spacing | 10 inches |
| Type of spayer | Tractor mounted boom sprayer |
| Tractor speed | 2.73 mph |
| Plot size | 45 × 10 ft. |
| No. of treatments | 31 |

TABLE V-continued

| | |
|---|---|
| No. of replications | 3 |
| Total No. of plots | 93 |
| Stage of weed growth | 4-6" high |
| Major weeds | Broadleaf weeds: |
| | camphor weeks |
| | Florida pusley |
| | Jerusalem oak |
| | lambsquarters |
| | pigweed |
| | Spanish needles |
| | tea weed |

The application was carried out in one day from 8 am to 5 pm.

Table III shows the number of days of treatment of Bahia grass. The first four tests indicate treatment with the wetting agents alone, the next test being an application of Ignite without any wetting agent. Tests 6 through 11 show the results with the inventive wetting agents SA1 and SA2. Tests 12 through 17 are comparative examples.

From the listed results, it is clear that the inventive compositions are at least as effective and in many instances more effective than, the comparative wetting agents.

Test 18 utilized fusilade alone, with tests 19 through 24 incorporating the inventive wetting agent in various concentrations. Tests 25 through 30 are comparative examples. Again the results establish that the inventive wetting agent is at least as effective, and in some instances more effective than, the comparative wetting agents.

Table IV shows similar results in testing for Broadleaf control and it is evident from the results that in many instances where Ignite was the herbicide of choice, the inventive wetting agents were comparable to or increased the effectiveness of the formulation. Fusilade, being a systemic herbicide, was not effective on Broadleaf weeds, regardless of the wetting agent used.

The results of Experiment 1 show that none of the wetting agents were phytotoxic to any weed species present in the experimental field. SA1 was slightly more effective than SA2 with both Ignite and Fusilande. Both were superior at concentrations of 0.25% over 0.0625% and 0.125%. The test species chosen in Table III, the Bahia grass, is a perennial grass and maximum control with Ignite was achieved 21 days after treatment and was maintained up to 42 days at which time regrowth and control percent dropped. Fusilade provided maximum control at 85% but maintained up to 63 days which is to be expected since this is a systemic herbicide.

The results shown in Table IV for Broadleaf weeds, show that there was no activity for fusilade on the Broadleafs. On the other hand, Ignite provided up to 100% control of Broadleaf weeds within 21 days after spraying. Since it is a contact herbicide, it kills weeds present only at the time of spraying. New weeds emerged later and control percent later dropped. The results clearly show that the inventive wetting agents, are at least as effective, and slightly more effective in promoting enhanced activity of the formulated herbicide than the comparative compounds.

EXPERIMENT 2

In this experiment, the inventive formulations SS1 and SS2 additionally included a sticking agent to enhance sticking of the herbicide formulation to the targeted organism. The sticking agents are preferably water soluble film forming agents, which are typically water soluble polymers such as vinyl pyrollidone/vinyl acetate copolymer 60:40, VP:VA, having a weight average molecular weight of 50,000, or a grafted copolymer such as polyvinyl pyrollidone containing 10% by weight butene. Of course, other sticking agents could also be used. In these experiments, phosphonomethyl glycine as its isopropyl amine salt, Glyphosate (Roundup) and Paraquat (Gramoxone) 1:1-Dimethyl-4,4' bipyridinium dichloride, a contact herbicide, were the selected active formulation ingredients. These same herbicides were combined with a known wetting agent, COMPLEX, containing alkylpolyoxyethylene ethers, polymerized resins and fatty acids 16.6%, reacted amines 5.2%, aromatic petroleum solvent 4.9%, inert ingredients 72.3%, manufactured by Riverside Chemical Co. The results are shown in Tables VI and VII. The evaluation of the formulations used on Bahia grass are shown in Table VI and on Broadleaf weeds in Table VII.

In Table VI, the first four tests indicate treatment with the wetting agents alone, the next test being an application of Roundup without any wetting agent. Tests 5 through 10 show the results with the inventive wetting/sticking agents SS1 and SS2. Tests 11 through 13 are comparative examples.

Test 14 utilized Paraquat without any wetting agent, tests 15 through 20 show the results with the inventive wetting agents and tests 21 through 23 were comparative examples.

Table VII shows similar results for Broadleaf weed control and it is evident that in many instances, the inventive wetting agent was comparable to the commercial wetting agents and in some instances increased herbicidal effectiveness.

TABLE VI

| Treatments: | DAYS AFTER TREATMENT CONTROL % | | | | |
|---|---|---|---|---|---|
| | 3 | 7 | 21 | 42 | 63 |
| 1. SS1 0.25% | 0 | 0 | 0 | 0 | 0 |
| 2. SS2 0.25% | 0 | 0 | 0 | 0 | 0 |
| 4. Complex 0.25% | 0 | 0 | 0 | 0 | 0 |
| 5. Glyphosate 1.0 lb ai/A | 5 | 25 | 50 | 40 | 25 |
| 6. Glyphosate 1.0 lb ai/A SS1 0.0625% | 5 | 30 | 80 | 55 | 50 |
| 7. Glyphosate 1.0 lb ai/A + SS1 0.125% | 5 | 30 | 90 | 65 | 60 |
| 8. Glyphosate 1.0 lb ai/A + SS1 0.25% | 5 | 50 | 100 | 80 | 90 |
| 9. Glyphosate 1.0 lb ai/A + SS2 0.0625% | 5 | 25 | 80 | 50 | 40 |
| 10. Glyphosate 1.0 lb ai/A + SS2 0.125% | 5 | 25 | 80 | 60 | 50 |
| 11. Glyphosate 1.0 lb ai/A + SS2 0.25% | 5 | 40 | 100 | 80 | 90 |
| 15. Glyphosate 1.0 lb ai/A + Complex 0.0625% | 5 | 25 | 60 | 40 | 25 |
| 16. Glyphosate 1.0 lb ai/A + Complex 0.125% | 5 | 25 | 70 | 40 | 25 |
| 17. Glyphosate 1.0 lb ai/A + Complex 0.25% | 5 | 30 | 90 | 60 | 80 |
| 18. Paraquat 0.625 lb ai/A | 50 | 50 | 40 | 30 | 10 |
| 19. Paraquat 0.625 lb ai/A + SS1 0.0625% | 70 | 70 | 60 | 40 | 10 |
| 20. Paraquat 0.625 lb ai/A + SS1 0.125% | 90 | 90 | 80 | 60 | 20 |
| 21. Paraquat 0.625 lb ai/A + SS1 0.25% | 100 | 100 | 95 | 75 | 50 |
| 22. Paraquat 0.625 lb ai/A + SS2 0.0625% | 75 | 75 | 70 | 30 | 10 |
| 23. Paraquat 0.625 lb ai/A + SS2 0.125% | 80 | 80 | 75 | 50 | 20 |

TABLE VI-continued

| Treatments: | DAYS AFTER TREATMENT CONTROL % | | | | |
|---|---|---|---|---|---|
| | 3 | 7 | 21 | 42 | 63 |
| 24. Paraquat 0.625 lb-ai/A + SS2 0.25% | 100 | 100 | 95 | 75 | 50 |
| 28. Paraquat 0.625 lb ai/A + Complex 0.0625% | 80 | 80 | 60 | 30 | 10 |
| 29. Paraquat 0.625 lb ai/A + Complex 0.125% | 80 | 80 | 60 | 30 | 10 |
| 30. Paraquat 0.625 lb ai/A + Complex 0.25% | 90 | 90 | 80 | 60 | 40 |
| 31. Untreated control | 0 | 0 | 0 | 0 | 0 |

TABLE VII

| Treatments: | DAYS AFTER TREATMENT CONTROL % | | | | |
|---|---|---|---|---|---|
| | 3 | 7 | 21 | 42 | 63 |
| 1. SS1 0.25% | 0 | 0 | 0 | 0 | 0 |
| 2. SS2 0.25% | 0 | 0 | 0 | 0 | 0 |
| 4. Complex 0.25% | 0 | 0 | 0 | 0 | 0 |
| 5. Glyphosate 1.0 lb ai/A | 5 | 10 | 50 | 20 | 10 |
| 6. Glyphosate 1.0 lb ai/A SS1 0.0625% | 5 | 20 | 75 | 40 | 15 |
| 7. Glyphosate 1.0 lb ai/A + SS1 0.125% | 5 | 25 | 75 | 40 | 15 |
| 8. Glyphosate 1.0 lb ai/A + SS1 0.25% | 10 | 50 | 100 | 60 | 25 |
| 9. Glyphosate 1.0 lb ai/A + SS2 0.0625% | 5 | 15 | 70 | 30 | 15 |
| 10. Glyphosate 1.0 lb ai/A + SS2 0.125% | 5 | 20 | 70 | 30 | 15 |
| 11. Glyphosate 1.0 lb ai/A + SS2 0.25% | 10 | 50 | 100 | 60 | 25 |
| 15. Glyphosate 1.0 lb ai/A + Complex 0.0625% | 5 | 15 | 60 | 25 | 10 |
| 16. Glyphosate 1.0 lb ai/A + Complex 0.125% | 5 | 15 | 65 | 30 | 10 |
| 17. Glyphosate 1.0 lb ai/A + complex 0.25% | 5 | 45 | 90 | 50 | 20 |
| 18. Paraquat 0.625 lb ai/A | 50 | 50 | 30 | 10 | 5 |
| 19. Paraquat 0.625 lb ai/A + SS1 0.0625% | 60 | 60 | 40 | 20 | |
| 20. Paraquat 0.625 lb ai/A + SS1 0.125% | 75 | 75 | 50 | 30 | 5 |
| 21. Paraquat 0.625 lb ai/A + SS1 0.25% | 100 | 100 | 80 | 50 | 10 |
| 22. Paraquat 0.625 lb ai/A + SS2 0.0625% | 55 | 55 | 40 | 20 | 5 |
| 23. Paraquat 0.625 lb ai/A + SS2 0.125% | 65 | 65 | 45 | 25 | 5 |
| 24. Paraquat 0.625 lb ai/A + SS2 0.25% | 100 | 100 | 80 | 50 | 10 |
| 28. Paraquat 0.625 lb ai/A + Complex 0.0625% | 50 | 50 | 40 | 15 | 5 |
| 29. Paraquat 0.625 lb ai/A + Complex 0.125% | 55 | 55 | 45 | 25 | 5 |
| 30. Paraquat 0.625 lb ai/A + Complex 0.25% | 90 | 90 | 60 | 40 | 5 |
| 31. Untreated control | 0 | 0 | 0 | 0 | 0 |

The data shown in Tables VI and VII show that none of these surfactants were phytotoxic to weeds by themselves. The SS1 formulation appeared to be better than SS2 with Roundup, but all surfactants were equally effective with Paraquat. In all cases, the concentration of 0.25% was more effective than the 0.0625% or 0.125%. Both SS1 and SS2 with both Roundup and Paraquat provided control at 0.25% concentration for Bahia grass as well as for Broadleaf weeds. Since Bahia grass is perennial, control was higher at the end of the test (63 days) than for Broadleaf weeds. Because Broadleaf weeds are annuals, once the existing weeds were killed, new weeds emerged and the rating dropped to reflect the presence of this new growth.

As is seen from the tables, the inventive wetting agents were at least as effective as and in many instances more effective in enhancing herbicide activity as compared to the comparative compound. Similar results were obtained when the inventive surfactants were utilized with the following formulations: ultra low volume sulfonylurea type actives using Pinnacle (25DF), Classic (25DF), Reflex (2LC) (Fomesafen) and also when compared to wetting agents such as Activate plus, Plex and Silicone. See Table VIII for formulations and rates used. In each instance, the inventive wetting agent was at least comparable to and in some instances superior to the comparative wetting agent in enhancing formulation effectiveness.

TABLE VIII

COMMERCIAL FORMULATIONS & RATES USED

| Commercial Formulation | Table | Active Ingredient | Conc. | Rate applied |
|---|---|---|---|---|
| Glyfosinate | III, IV | Ammonium (3 amino-3-carboxypropyl)-methyl phosphinate | 2 lbs Emulsifiable concentrate/gal | 0.5 lb/acre or 0.5 lb/20 gal |
| Fluazifop-p-butyl | III | Butyl 2[4-(5-trifluoro methyl-2-pyridyloxy) phenoxy] propionate | 2 lbs Mulsifiable concentrate/gal | 0.25 lb/acre or 0.25 lb/20 gal |
| Glyphosate | VI, VII | Isopropylamine salt of N-phosphono methyl glycine | 4 lbs Liquid Concentrate/gal | 1.0 lbs/acre or 1 lb/20 gal |
| Paraquat | IV, V | 1:1-Dimethyl-4,4¹-Bipyridinium dichloride | | 0.625 lb. acre or 0.625 lb/20 gal |
| Pinnacle | — | Methyl 3[[4-methoxy-6-methyl-1,3,5-triazine-2-yl) amino-carbonyl] amino sulfonyl]-2-thiophene carboxylate | 25% Dry flowable | 0.25 oz. per acre 0.25 oz in 20 gal |
| Classic | — | 2-(([4-chloro-6-methoxy pyrimidine-2yl) amino carbonyl] amino-sulfonyl benzoic acid, ethyl ester | 25% Dry flowable | 0.25 oz acre 0.25 oz in 20 gal |
| Reflex | — | 5-[2-chloro-4-(trifluoro-methyl) phenoxy]-N-(methyl-sulfonyl)-2-nitrobenza-mide | 2 lbs Liquid concentrate/gal | 0.03125, 0.0625, 0.125 and 0.25 LAS/arce or in 120 gal. |

TABLE IX

COST PERFORMANCE DATA

| | Active Conc. (%) | Wetting time (Sec.) |
|---|---|---|
| Pulse (Silwett L-77) | 0.3 | 4 |
| Recommended Concentration: (0.03%–0.3%) | 0.15 | 7 |
| | 0.1 | 11 |
| | 0.06 | 18 |

TABLE IX-continued

| | COST PERFORMANCE DATA | |
|---|---|---|
| | Active Conc. (%) | Wetting time (Sec.) |
| | 0.03 | 36 |
| SA1 Formulation | 0.5 | <1 |
| Recommended Concentration: | 0.3 | <1 |
| (0.06%–0.5%) | 0.15 | 2 |
| | 0.1 | 4 |
| | 0.06 | 35 |

Utilizing the inventive formulations, various herbicides and pesticides can be applied at low costs with high effectiveness.

Referring to Table IX, cost performance for the inventive formulation in comparison to commercially available formulation can be calculated. For example, at 0.3%, the inventive formulation is approximately ½ the cost of the commercial material, and achieves a quicker wetting time. For example, using 0.1% of the inventive wetting agent yields the same wetting time as 0.3% of the comparable material. Generally, from 0.05–1.0% of the inventive formulation is added to the active ingredient, preferably 0.06–0.5% and most preferably 0.2–0.4%.

EXPERIMENT 3

A modified Draves wetting test was conducted with a 0.7 gram cotton skein, and 0.9 gram weight. A comparison was made between the inventive formulations SA1, SA2, SS1, SS2, modified SA1, modified SA2, modified SS2, commercial formulations using Activate Plus, nonoxynol-9 and Pulse according to modified ASTMD 2281-68; 15.04 (1990) Draves wetting test.

TABLE X

| Product | Concentrations % Wetting time in seconds | | | | | | | | | | | |
|---|---|---|---|---|---|---|---|---|---|---|---|---|
| | 0.01 | 0.05 | 0.075 | 0.1 | 0.15 | 0.2 | 0.25 | 0.3 | 0.5 | 0.6 | 0.75 | 1.0 |
| SA1 | >1 hr | >1 hr | >1 hr | 21.9 | 5.53 | 3.0 | 0 | 0 | 0 | 0 | 0 | 0 |
| SA2 | >1 hr | >1 hr | 49 | 28 | 5.5 | 3.3 | 2.0 | 0 | 0 | 0 | 0 | 0 |
| SS1 | >1 hr | >1 hr | 441 | 27.5 | 5.9 | 3.0 | 0 | 0 | 0 | 0 | 0 | 0 |
| SS2 | >1 hr | >1 hr | >1 hr | 20 | 5.0 | 3.0 | 0 | 0 | 0 | 0 | 0 | 0 |
| Modified SA1 | >1 hr | >1 hr | 15.80 | 94.4 | 11.0 | 8.0 | 4.7 | 4.0 | 0 | 0 | 0 | 0 |
| Modified SA2 | >1 hr | >1 hr | 122 | 49.6 | 15.5 | 10.0 | 5.5 | 4.0 | 3.3 | 0 | 0 | 0 |
| Modified SS2 | >1 hr | >1 hr | 127 | 50.0 | 15.3 | 10.3 | 6.5 | 4.2 | 3.1 | 0 | 0 | 0 |
| Activate Plus | >1 hr | 408 | 116 | 79.0 | 38.7 | 27.0 | 21.7 | 19.3 | 13.3 | 12.0 | 9.9 | 8.4 |
| Nonoxynol-9 | >1 hr | 35 | — | 13.0 | — | 4.0 | 4.0 | 4.0 | 2.0 | 2.0 | 2.0 | 1.0 |
| Pulse | 420 | 103 | — | 7.0 | — | 4.0 | 3.0 | 3.0 | 2.0 | 2.0 | 2.0 | 1.0 |

Table X shows the wetting time of test materials at various concentrations. Tests were discontinued if the wetting time exceeded one hour. From the results, it is seen that the inventive formulations are in many instances comparable to, if not better than, the comparative compounds.

Utilizing the inventive surfactant in a herbicide or pesticide formulation promotes and increases wetting with reduced cost. Consequently, the inventive formulations are considered an advance in the art.

While preferred embodiments of the present invention have been shown and described, it will be understood by those skilled in the art that various changes or modifications could be made without varying from the scope of the present invention. For example, it is expected that optional ingredients, such as non-ionic surfactants, may additionally be combined with the wetting agents of the invention.

What is claimed is:

1. A water base wetting agent for pesticide and herbicide formulations consisting essentially of 33 to 90% $C_6$–$C_{20}$ N-alkyl substituted lactam, 8 to 16% anionic surfactant and water.

2. The wetting agent of claim 1 wherein the alkyl lactam is of the following Formula I:

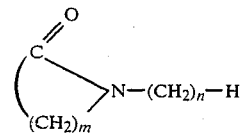

Where m = 3, 4, 5 and n 6–20.

3. The wetting agent of claim 1 wherein the alkyl substituted lactam is a pyrrolidone of the following formula:

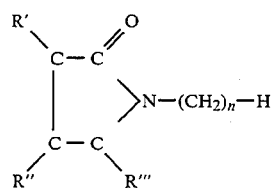

where n = 6–20 (branched or linear), R', R" and R''' are H, lower alkyl, alkoxyl cycloalkyl, or aralkyl.

4. The wetting agent of claim 3 wherein the pyrrolidone is from the group consisting of N-octyl-2 pyrrolidone, N-isooctyl pyrrolidone, N-dodecyl-2-pyrrolidone, N-octadecyl-2-pyrrolidone and mixtures thereof.

5. The wetting agent of claim 1 wherein the anionic surfactant is an alkali metal salt of $C_8$–$C_{22}$ aliphatic surfactants.

6. The wetting agent of claim 1 wherein the anionic surfactant is from the group consisting of sodium dodecyl sulfate, sulfonate, alkali metal salts of alkyl aromatic sulfonates, sulfates, and ethoxylated versions thereof.

7. The wetting agent of claim 1 wherein the anionic surfactant is sodium dodecyl sulfate.

8. The wetting agent of claim 1 wherein from 35–65% of the alkyl substituted lactam is present.

9. The wetting agent of claim 1 wherein from 39–55% of the alkyl substituted lactam is present.

10. The wetting agent of claim 1 wherein from 10–14% anionic surfactant is present.

11. The wetting agent of claim 1 further comprising an effective amount of a solvent for promoting homogeneity.

12. The wetting agent of claim 11 wherein the solvent is N-methyl pyrrolidone.

13. The wetting agent of claim 11 wherein from about 1 to about 20% of the solvent for promoting homogeneity is present.

14. The wetting agent of claim 1 further comprising an effective amount of a water soluble sticking agent.

15. The wetting agent of claim 14 wherein from about 1 to about 5% of the water soluble sticking agent is present.

16. The wetting agent of claim 14 wherein the water soluble sticking agent is a vinyl pyrrolidone/vinyl acetate copolymer.

17. The wetting agent of claim 14 wherein the water soluble sticking agent is a graft polymer of polyvinyl pyrrolidone containing butene.

18. A method for treating plants comprising:
provinding a water based wetting agent consisting essentially of 33–90% $C_6$–$C_{20}$ N-alkyl substituted lactam, 8 to 16% anionic surfactant, and water;
adding from 0.05 to 1% of the wetting agent to an aqueous pesticide or herbicide formulation and,
contacting the admixed formulation with the plants.

* * * * *